(12) United States Patent
Agha

(10) Patent No.: US 9,084,842 B1
(45) Date of Patent: Jul. 21, 2015

(54) DERMAL FILLER COMPOSITION

(71) Applicant: Rania Agha, Desplaines, IL (US)

(72) Inventor: Rania Agha, Desplaines, IL (US)

( * ) Notice: Subject to any disclaimer, the term of this patent is extended or adjusted under 35 U.S.C. 154(b) by 0 days.

(21) Appl. No.: 13/888,651

(22) Filed: May 7, 2013

Related U.S. Application Data

(60) Provisional application No. 61/643,600, filed on May 7, 2012.

(51) Int. Cl.
| | | |
|---|---|---|
| *A61L 27/50* | (2006.01) | |
| *A61L 27/20* | (2006.01) | |
| *A61K 8/73* | (2006.01) | |
| *A61K 8/19* | (2006.01) | |
| *A61K 8/29* | (2006.01) | |
| *A61K 33/00* | (2006.01) | |

(52) U.S. Cl.
CPC ............... *A61L 27/50* (2013.01); *A61L 27/20* (2013.01); *A61K 8/19* (2013.01); *A61K 8/29* (2013.01); *A61K 8/735* (2013.01); *A61K 33/00* (2013.01); *A61L 2400/06* (2013.01)

(58) Field of Classification Search
None
See application file for complete search history.

(56) References Cited

U.S. PATENT DOCUMENTS

2004/0202625 A1* 10/2004 Daniloff et al. ................. 424/63
2010/0100179 A1* 4/2010 Hubbard ......................... 623/8

FOREIGN PATENT DOCUMENTS

FR 2919999 * 8/2007

OTHER PUBLICATIONS

Machine translation of FR 2919999 (2007).*

\* cited by examiner

*Primary Examiner* — Leigh Maier
(74) *Attorney, Agent, or Firm* — Alvin T. Rockhill

(57) ABSTRACT

The present invention relates to an injectable dermal filler composition that can be injected into the skin of the orbital trough of a patient without aggravating darkness around the eyes of the patient. In fact, this composition can be used to lighten such dark areas which have developed over time. The present invention more specifically discloses an injectable dermal filler composition comprising hyaluronic acid and a white colorant. The present invention further reveals a method for treating wrinkles and firming an area of skin on a human patient comprising injecting an injectable dermal filler composition comprising hyaluronic acid and a white colorant, into the area of skin on the human patient.

10 Claims, No Drawings

DERMAL FILLER COMPOSITION

This application claims benefit of U.S. Provisional Patent Application Ser. No. 61/643,600, filed on May 7, 2012. The teachings of U.S. Provisional Patent Application Ser. No. 61/643,600 are incorporated herein by reference in their entirety.

BACKGROUND OF THE INVENTION

Injectable dermal fillers are widely used by dermatologists and plastic surgeons to soften deep folds and reduce wrinkles on the faces of patients, such as lines from the nose to the corners of the mouth and "crows feet" which extend from the corners of the mouth. They are also commonly used as a lip augmentation agent and to fill in hollow places and scars on the face.

The injectable dermal fillers used in such applications are typically comprised of hyaluronic acid because it can absorb up to 1000 times its own weight in water which accordingly adds volume under the surface of sagging skin to provide a more youthful appearance. Hyaluronic acid is also believed to bind to collagen present in the skin to enhance firming. There is some evidence that hyaluronic acid stimulates additional collagen formation which is highly advantageous since collagen supports the skin structure.

Dermal fillers can also be injected into the skin of the orbital trough of a patient to firm the skin in the area around the eyes. However, this procedure is complicated by the fact that some people develop dark circles around their eyes with age. The injection of dermal fillers aggravates this problem and can cause such dark areas to have an even darker appearance due to the Tyndall effect. This is caused by the filler particles scattering the light in a manner that results in a darker appearance (black or dark blue). Accordingly, the use of dermal fillers in the orbital trough of patients that have developed dark circles around their eyes can be problematic.

SUMMARY OF THE INVENTION

The present invention is relates to an injectable dermal filler composition that can be injected into the skin of the orbital trough of a patient without aggravating darkness around the eyes of the patient. In fact, this composition can be used to lighten such dark areas which have developed over time. The present invention more specifically discloses an injectable dermal filler composition comprising hyaluronic acid and a white colorant.

The present invention further reveals a method for treating wrinkles and firming an area of skin on a human patient comprising injecting an injectable dermal filler composition comprising hyaluronic acid and a white colorant, into an area of skin on the human patient.

DETAILED DESCRIPTION OF THE INVENTION

The injectable dermal filler composition of this invention is comprised of hyaluronic acid and a white colorant. The hyaluronic acid will typically be crosslinked and will normally be in the form of a gel. Hyaluronic acid which is suitable for use in the practice of this invention is commercially available as Juvederm™, Restylane™, and Perlane™

The white colorant will preferably be non-toxic. Some representative examples of white colorants that can be used include: lead carbonate, titanium dioxide, barium sulfate, zinc oxide, calcium carbonate, calcium oxide, calcium adipate, calcium adipate monohydrate, calcium gluconate, calcium citrate, calcium lactate, and calcium phosphate. The white colorant will preferably be a calcium compound, such as calcium carbonate, calcium adipate, calcium adipate monohydrate, calcium gluconate, calcium citrate, calcium lactate, or calcium phosphate.

The white colorant will typically be present in the injectable dermal filler composition of this invention at a level which is within the range of about 1 weight percent to about 40 weight percent, based upon the total weight of the injectable filler composition. The white colorant will more typically be present in the injectable filler composition at a level which is within the range of about 2 weight percent to about 35 weight percent, based upon the total weight of the injectable filler composition. For instance the white colorant can be present in the injectable filler composition at a level which is within the range of about 5 weight percent to about 30 weight percent, based upon the total weight of the injectable filler composition. The white colorant can also be present in the injectable filler composition at a level which is within the range of about 10 weight percent to about 25 weight percent, based upon the total weight of the injectable filler composition. In another scenario, the white colorant can be present in the injectable filler composition at a level which is within the range of about 10 weight percent to about 20 weight percent, based upon the total weight of the injectable filler composition.

The injectable dermal filler composition of this invention can optionally further include a yellow colorant. Some representative examples of yellow colorant that can be used include: cadmium yellow, ochres, curcuma yellow, chrome yellow, and disazodiarylide. It is normally preferred for the injectable dermal filler composition of this invention to also contain lidocaine.

In accordance with this invention, the injectable dermal filler composition of this invention is injected into an area of skin on the human patient. This area will typically be within the orbital trough of the patient, such as the area under the eyes of the patient. The amount of the injectable dermal filler composition injected will typically be within the range of about 0.25 ml to about 2 ml. The amount of the injectable dermal filler composition injected will more typically be within the range of about 0.25 ml to about 1.5 ml. For instance, the amount of the injectable dermal filler composition injected can be within the range of about 0.5 ml to about 1.5 ml. The amount of the injectable dermal filler composition injected can also be within the range of about 0.5 ml to about 1.25 ml or it can be within the range of about 0.75 ml to about 1.25 ml. In many cases the amount of dermal filler composition injected will be within the range of about 0.75 ml to about 1 ml.

What is claimed is:

1. An injectable dermal filler composition comprising hyaluronic acid, wherein the hyaluronic acid is crosslinked, a white colorant, and a yellow colorant selected from the group consisting of cadmium yellow, ochres, and chrome yellow.

2. The injectable filler composition as specified in claim 1 wherein the hyaluronic acid is in the form of a gel.

3. The injectable filler composition as specified in claim 1 wherein the white colorant is non-toxic.

4. The injectable filler composition as specified in claim 1 wherein the white colorant is selected from the group consisting of lead carbonate, titanium dioxide, barium sulfate, zinc oxide, calcium carbonate, calcium oxide, calcium adipate, calcium adipate monohydrate, calcium gluconate, calcium citrate, calcium lactate, and calcium phosphate.

5. The injectable filler composition as specified in claim 1 wherein the white colorant is present in the injectable filler composition at a level which is within the range of about 1 weight percent to about 40 weight percent, based upon the total weight of the injectable filler composition.

6. The injectable filler composition as specified in claim 1 wherein the white colorant is present in the injectable filler composition at a level which is within the range of about 2 weight percent to about 35 weight percent, based upon the total weight of the injectable filler composition.

7. The injectable filler composition as specified in claim 1 wherein the white colorant is present in the injectable filler composition at a level which is within the range of about 5 weight percent to about 30 weight percent, based upon the total weight of the injectable filler composition.

8. The injectable filler composition as specified in claim 1 wherein the white colorant is present in the injectable filler composition at a level which is within the range of about 10 weight percent to about 25 weight percent, based upon the total weight of the injectable filler composition.

9. The injectable filler composition as specified in claim 1 wherein the white colorant is present in the injectable filler composition at a level which is within the range of about 10 weight percent to about 20 weight percent, based upon the total weight of the injectable filler composition.

10. The injectable filler composition as specified in claim 1 wherein the injectable filler composition is further comprised of lidocaine.

\* \* \* \* \*